United States Patent
Chakrabarti et al.

(10) Patent No.: US 10,723,685 B2
(45) Date of Patent: Jul. 28, 2020

(54) PROCESS FOR PREPARING METHACROLEIN

(71) Applicant: Rohm and Haas Company, Collegeville, PA (US)

(72) Inventors: Reetam Chakrabarti, Phoenixville, PA (US); Dmitry A. Krapchetov, Lansdale, PA (US); Mark A. Silvano, Upper Black Eddy, PA (US); Jinsuo Xu, Berwyn, PA (US)

(73) Assignee: Rohm and Haas Company, Collegeville, PA (US)

( * ) Notice: Subject to any disclaimer, the term of this patent is extended or adjusted under 35 U.S.C. 154(b) by 0 days.

(21) Appl. No.: 16/615,841

(22) PCT Filed: May 24, 2018

(86) PCT No.: PCT/US2018/034271
§ 371 (c)(1),
(2) Date: Nov. 22, 2019

(87) PCT Pub. No.: WO2018/217961
PCT Pub. Date: Nov. 29, 2018

(65) Prior Publication Data
US 2020/0140363 A1    May 7, 2020

Related U.S. Application Data

(60) Provisional application No. 62/510,984, filed on May 25, 2017.

(51) Int. Cl.
*C07C 45/82* (2006.01)
*C07C 47/22* (2006.01)
*C07C 45/75* (2006.01)

(52) U.S. Cl.
CPC .............. *C07C 47/22* (2013.01); *C07C 45/75* (2013.01); *C07C 45/82* (2013.01); *C07C 2531/04* (2013.01)

(58) Field of Classification Search
CPC ................................ C07C 45/75; C07C 45/82
See application file for complete search history.

(56) References Cited

U.S. PATENT DOCUMENTS

| | | |
|---|---|---|
| 3,821,286 A | 6/1974 | Pai et al. |
| 4,427,486 A | 1/1984 | Green et al. |
| 4,496,770 A | 1/1985 | Duembgen et al. |
| 4,716,250 A | 12/1987 | Abatjoglou et al. |
| 4,731,486 A | 3/1988 | Abatjoglou et al. |
| 5,087,763 A | 2/1992 | Sorensen |
| 5,288,916 A | 2/1994 | Lorenz et al. |
| 7,141,702 B2 | 11/2006 | Deshpande et al. |
| 7,999,133 B2 | 8/2011 | Stevenson et al. |
| 8,716,523 B2 | 5/2014 | Sudo et al. |
| 9,751,822 B2 | 9/2017 | Kurakami et al. |
| 2016/0051970 A1 | 2/2016 | Sakai et al. |
| 2016/0068464 A1 | 3/2016 | Krill et al. |
| 2016/0200660 A1 | 7/2016 | Krill et al. |
| 2016/0229779 A1 | 8/2016 | Hoy, IV et al. |

*Primary Examiner* — Sikarl A Witherspoon
(74) *Attorney, Agent, or Firm* — Brian L. Mutschler

(57) ABSTRACT

Provided is a process for preparing methacrolein which maximizes capture of methanol. Also provided are processes for producing methacrylic acid and methyl methacrylate.

10 Claims, 1 Drawing Sheet

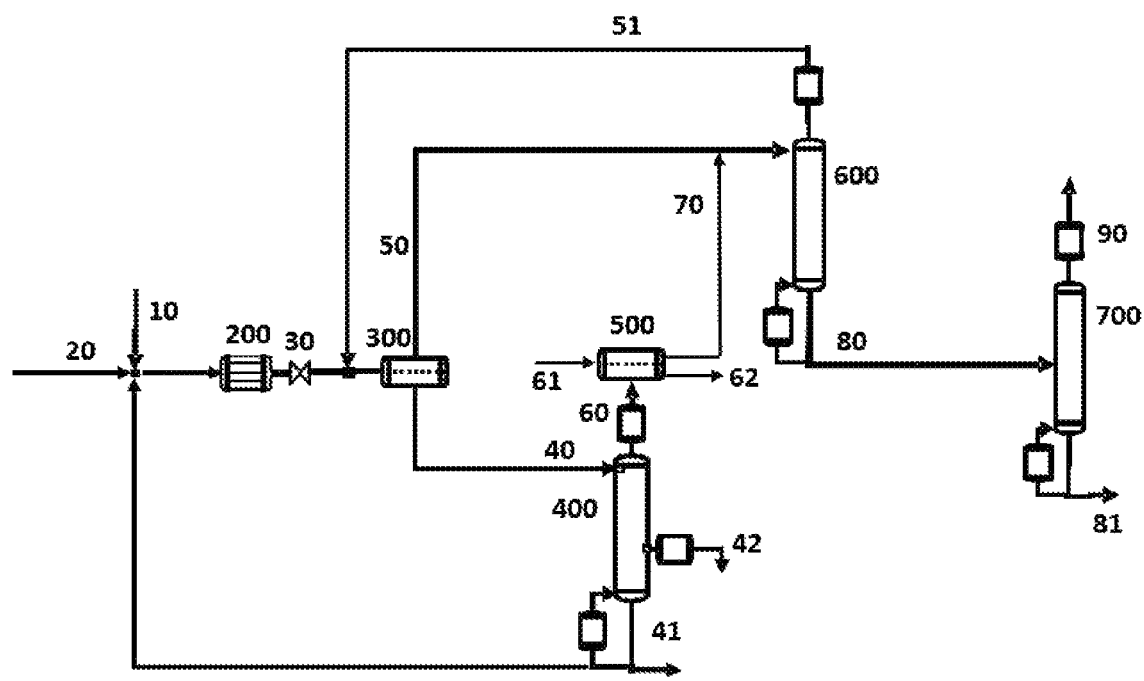

PROCESS FOR PREPARING METHACROLEIN

FIELD OF THE INVENTION

This invention relates to a process for preparing dry methacrolein, and to processes for making methacrylic acid and methyl methacrylate.

BACKGROUND

Methacrolein (2-methylprop-2-enal; "MA") is a common intermediate in methacrylic acid ("MAA") production. MA can be produced from ethylene ($C_2$) feedstock, such as via liquid phase propionaldehyde condensation as disclosed in U.S. Pat. No. 4,496,770. The MA product stream contains methanol that is supplied with formaldehyde that is used in the propionaldehyde condensation. Such methanol can be detrimental in a subsequent oxidation process, which converts MA in the presence of oxygen to MAA in a single step. Thus, a MA stream from conventional processes must be sufficiently free of methanol to be used as a feed stream for a downstream oxidation process, in addition to having a substantial absence of certain impurities (e.g., propionaldehyde, formaldehyde, acetic acid, and organic heavies including, but not limited to, propionic acid, methacrolein dimer, 2-methyl-2-pentenal, and other methacrolein oligomers) that can have a negative effect on efficiency of the oxidation process.

Processes for preparing dry MA have been described in the art. For example, US 2016/0229779 discloses a process comprising (a) providing a wet MA stream containing MA, methanol, and at least 8 weight % water to a phase separator, (b) separating the MA stream into organic and aqueous phases, (c) distilling the organic phase to produce a product stream containing MA and a first overhead stream, (d) sending the first overhead stream back to the phase separator, and (e) distilling the aqueous phase to produce a second overhead stream that is recycled back to the phase separator. The prior art does not, however, disclose a process that further minimizes methanol content in the MA product stream for use in a downstream oxidation process, or further minimizes certain impurities that can negatively affect the efficiency of the oxidation process.

Accordingly, there is a need to develop processes for preparing MA prepared from an ethylene ($C_2$) feedstock, wherein the MA stream has a low methanol content suitable for use in a downstream oxidation process while also removing detrimental impurities.

STATEMENT OF INVENTION

One aspect of the invention provides a process for preparing methacrolein comprising (a) mixing water and an amine-acid catalyst to provide a catalyst stream, (b) sending the catalyst stream and a reaction stream comprising propionaldehyde, formaldehyde, and methanol to a reactor to produce a first intermediate stream comprising methacrolein, methanol, and at least 8 weight % water, (c) providing the first intermediate stream to a first phase separator to produce (i) a first aqueous phase comprising methacrolein, methanol, amine-acid catalyst, and at least 65 weight % water, and (ii) a first organic phase comprising water, at least 85 weight % methacrolein, and less than 5 weight % methanol, (d) distilling the first aqueous phase in a first distillation column to produce (i) a second intermediate stream comprising methacrolein, water, and less than 60 weight % methanol, (ii) a bottoms stream comprising amine-acid catalyst, and (iii) a side draw stream comprising methanol and water, (e) providing the second intermediate stream and water to a second phase separator to produce (i) a second organic phase comprising methacrolein, water, and less than 55 weight % methanol, and (ii) a second aqueous phase, (f) distilling the first organic phase and the second organic phase in a second distillation column to produce (i) a third intermediate stream comprising methacrolein and less than 2 weight % methanol, and (ii) an overhead stream, (g) distilling the third intermediate stream in a third distillation column to produce (i) a product stream comprising methacrolein and water in a combined amount of at least 97 weight %, less than 2 weight % methanol, and less than 1 weight % of impurities comprising one or more of acetic acid, propionic acid, methacrolein dimer, and 2-methyl-2-pentenal, and (ii) a waste stream, (h) recycling at least part of the overhead stream to the first phase separator, and (i) recycling at least part of the bottoms stream to the catalyst stream.

BRIEF DESCRIPTION OF THE FIGURES

FIG. 1 is a schematic of an embodiment of the invention.

DETAILED DESCRIPTION

The inventors have now surprisingly found a process for preparing methacrolein ("MA") prepared from an ethylene ($C_2$) feedstock, wherein MA stream has a low methanol content suitable for use in a downstream oxidation process while also removing detrimental impurities.

One embodiment of the invention is shown in FIG. 1. A catalyst stream 10 is provided by mixing water and an amine-acid catalyst. In certain embodiments, the water and catalyst are mixed in a catalyst tank. The amine-acid catalyst is capable of catalyzing the Mannich condensation of propionaldehyde and formaldehyde to methacrolein. The Mannich condensation process is known in the art, for example, as described in U.S. Pat. No. 4,496,770 and U.S. Pat. No. 7,141,702. Suitable amine-acid catalysts include, for example, those comprising a secondary amine, e.g., dimethylamine, and an acid, e.g., acetic acid.

Suitable acids of the amine-acid catalysts include, for example, inorganic acids and organic mono-, di-, or polycarboxylic acids. Suitable carboxylic acids include, for example, aliphatic $C_1$-$C_{10}$ monocarboxylic acids, $C_2$-$C_{10}$ dicarboxylic acids, $C_2$-$C_{10}$ polycarboxylic acids. In certain embodiments, the acid comprises at least one of acetic acid, propionic acid, methoxyacetic acid, n-butyric acid, isobutyric acid, oxalic acid, succinic acid, tartaric acid, glutaric acid, adipic acid, maleic acid, fumaric acid, and combinations thereof. Suitable inorganic acids include, for example, sulfuric acid and phosphoric acid.

Suitable amines of the amine-acid catalysts include, for example, those of the formula $NHR^2R^3$, where $R^2$ and $R^3$ are each independently $C_1$-$C_{10}$ alkyl, which are optionally substituted with an ether, hydroxyl, secondary amino or tertiary amino group, or $R^2$ and $R^3$, together with the adjacent nitrogen, may form a $C_5$-$C_7$ heterocyclic ring, optionally containing a further nitrogen atom and/or an oxygen atom, and which are optionally substituted by a $C_1$-$C_4$ alkyl or $C_1$-$C_4$ hydroxyalkyl. In certain embodiments, the amine comprises at least one of dimethylamine, diethylamine, methylethylamine, methylpropylamine, dipropylamine, dibutylamine, diisopropylamine, diisobutylamine, methylisopropylamine, methylisobutylamine, methyl-sec.-butylamine, methyl-(2-methylpentyl)-amine, methyl-(2-ethylhexyl)-amine, pyrrolidine, piperidine, morpholine, N-methylpiperazine, N-hydroxyethylpiperazine, piperazine, hexamethyleneimine, diethanolamine, methylethanolamine, methylcyclohexylamine, methylcyclopentylamine, and dicyclohexylamine, and combinations thereof.

In certain embodiments, the amine-acid catalyst comprises dimethylamine and acetic acid. In certain embodiments, the molar ratio of the amine to acid is such that the resulting pH is from 2.5 to 7. For example, in certain embodiments the amine-acid catalyst contains a molar ratio of dimethylamine to acetic acid in an amount of from 10:1 to 1:10, preferably of from 5:1 to 1:5, and more preferably of from 1:1 to 1:1.2.

The Mannich condensation reaction is carried out by sending the catalyst stream 10 and a reaction stream 20 containing propionaldehyde, formaldehyde, and methanol to a reactor 200 to produce a first intermediate stream 30 containing methacrolein, methanol, and water via the Mannich condensation reaction. The reaction can be carried out under any suitable conditions at which the reaction proceeds. For example, the reaction can be conducted at a temperature of at least 20° C. and at least atmospheric pressure. In certain embodiments, the reaction is conducted in the liquid phase at above 100° C., e.g., 150-220° C., and at superatmospheric pressure, e.g., 10-80 bar. The molar ratio of propionaldehyde to formaldehyde is not particularly limited. For example, in certain embodiments the reaction stream 20 contains a ratio of propionaldehyde to formaldehyde in an amount of from 1.1:1 to 1:2, preferably of from 1.1:1 to 1:1.5, and more preferably of from 1.05:1 to 1:1.05. The first intermediate stream 30 is considered a "wet" methacrolein stream in that it comprises at least 8 weight %, or at least 10 weight % water, or at least 20 weight % water, or at least 40 weight % water, based on the total weight of the first intermediate stream 30. In certain embodiments, the methanol and formaldehyde present in the reaction stream 20 are provided in the form of formalin. In certain embodiments, the formalin utilized in the process of the invention is a saturated water solution containing formaldehyde in an amount of about 37 weight %, and methanol in an amount of from 10 to 15 weight %, based on the total weight of the formalin. The methanol present in the formalin can be detrimental in a subsequent oxidation process, which converts methacrolein in the presence of oxygen to methacrylic acid. The inventors have surprisingly found that the efficient removal of methanol from the first intermediate feed stream 30 prior to its downstream use as a source for the subsequent oxidation process is beneficially achieved by the process of the current invention.

Accordingly, the first intermediate stream 30 is sent to a first phase separator 300 to produce an organic phase 50 and aqueous phase 40. The aqueous phase 40 contains methacrolein, methanol, amine-acid catalyst, and primarily water. In certain embodiments, water is present in the aqueous phase 40 in an amount of at least 65 weight %, preferably at least 75 weight %, and more preferably at least 80 weight %, based on the total weight of the aqueous phase 40.

The aqueous phase 40 is then distilled in a first distillation column 400 to produce a second intermediate stream 60, a bottoms stream 41, and a side draw stream 42. The second intermediate stream 60 contains water, methanol, and methacrolein. In certain embodiments, methanol is present in the second intermediate stream 60 in an amount of less than 60 weight %, preferably less than 40 weight %, and even more preferably less than 20 weight %, based on the total weight of the second intermediate stream 60. In certain embodiments, methacrolein and water are present in the second intermediate stream 60 in an amount of greater than 40 weight %, preferably greater than 60 weight %, and more preferably greater than 80 weight %, based on the total weight of the second intermediate stream 60. The bottoms stream 41 contains amine-acid catalyst of the catalyst stream 10 that is recovered through the process of the invention. In certain embodiments, at least part of the bottoms stream 41 is recycled to the catalyst stream 10, which in preferred embodiments is mixed in the catalyst tank 100. The side draw stream 42 contains primarily water and certain organic compounds from the process.

The second intermediate stream 60 and water 61 are then sent to a second phase separator 500 to produce a second organic phase 70 and a second aqueous phase 62. The second organic phase 70 contains methacrolein, water, and methanol. In certain embodiments, the methanol is present in the second organic phase 70 in an amount of less than 55 weight %, preferably less than 35 weight %, and more preferably less than 15 weight %, based on the total weight of the second organic phase 70. In certain embodiments, methacrolein and water are present in the second organic phase 70 in an amount of greater than 45 weight %, preferably greater than 65 weight %, and more preferably greater than 85 weight %, based on the total weight of the second organic phase 70. While not wishing to be bound by theory, it is believed that operating the second phase separator 500 at low temperatures results in the second organic phase 70 containing lower amounts of methanol, which is beneficial for the downstream distillation of the second organic phase 70. Accordingly, in certain embodiments the second phase separator 500 is operated at a temperature of less than 25° C., preferably less than 15° C., and more preferably less than 10° C. In certain embodiments, the ratio of the water 61 entering the second phase separator 500 to second intermediate stream 60 entering the second phase separator 500 is from 1:10 to 100:1, preferably from 3:10 to 10:1, and more preferably from 5:10 to 1:1.

The organic phase 50 contains water, methanol, and primarily methacrolein. In certain embodiments, the methacrolein is present in the organic phase 50 in an amount of at least 85 weight %, preferably at least 88 weight %, and more preferably at least 92 weight %, based on the total weight of the organic phase 50. In certain embodiments, the methanol is present in the organic phase 50 in an amount of less than 5 weight %, preferably less than 4 weight %, and more preferably less than 3 weight %, based on the total weight of the organic phase 50. While not wishing to be bound by theory, it is believed that operating the first phase separator 300 at low temperatures results in the organic phase 50 containing lower amounts of methanol, which is beneficial for the downstream distillation of the organic phase 50. Accordingly, in certain embodiments the first phase separator 300 is operated at a temperature of less than 15° C., preferably less than 10° C., and more preferably less than 5° C.

The first organic phase 50 and the second organic phase 70 are then distilled in a second distillation column 600 to produce a third intermediate stream 80 and an overhead stream 51. In certain embodiments, the second distillation column 600 is operated as a stripping column, wherein the overheads vapors are condensed without any liquid being refluxed back to the column. In certain embodiments, the ratio of the third intermediate stream 80 exiting the second distillation column 600 to the combined amount of the first organic phase 50 and second organic phase 70 entering the second distillation column 600 is from 1:10 to 9:10, preferably from 2:10 to 8:10, and more preferably from 3:10 to 7:10. The third intermediate stream 80 contains water, methanol, and primarily methacrolein. In certain embodiments, methanol is present in the third intermediate stream 80 in an amount of less than 2 weight %, preferably less than 1 weight %, and more preferably less than 0.5 weight %, based on the total weight of the third intermediate stream 80. In certain embodiments, methacrolein is present in the third intermediate stream 80 in an amount of at least 90 weight %, preferably 92 weight %, and more preferably 95 weight %, based on the total weight of the third intermediate stream 80. The overhead stream 51 contains water, methanol, and primarily methacrolein. In certain embodiments, at least part of the overhead stream 51 is recycled to the phase separator 300.

The third intermediate stream 80 is then distilled in a third distillation column 700 to produce a product stream 90 and a waste stream 81. The product stream 90 contains water, methanol, and primarily methacrolein. In certain embodiments, the methacrolein and water are present in the product stream 90 in an amount of at least 97 weight %, preferably at least 98 weight %, and more preferably at least 99 weight %, based on the total weight of the product stream 90. In certain embodiments, methanol is present in the product stream 90 in an amount of less than 2 weight %, preferably less than 1 weight %, and more preferably less than 0.5 weight %, based on the total weight of the product stream 90. The waste stream 81 contains undesired organic compounds from the process, e.g., methacrolein dimer, 2-methyl-2-pentenal, inhibitor, and other heavy organic compounds from the process.

Inhibitors can be introduced into the process through one or more locations, for example, the catalyst tank 100, the reactor 200, the first phase separator 300, the second phase separator 500, the first distillation column 400, the second distillation column 600, the third distillation column 700, the overhead stream 51, and the product stream 90. Suitable inhibitors include, for example, 4-hydroxy-2,2,6,6-tetramethylpiperidin-1-oxyl (4-Hydroxy-TEMPO).

In certain embodiments, the propionaldehyde in the reaction stream 10 is prepared by the hydroformylation of ethylene. The hydroformylation process is known in the art, for example, as described in U.S. Pat. Nos. 4,427,486, 5,087,763, 4,716,250, 4,731,486, and 5,288,916. The hydroformylation of ethylene to propionaldehyde involves contacting ethylene with CO and hydrogen in the presence of a hydroformylation catalyst. Suitable hydroformylation catalysts include, for example, metal-organophosphorous ligand complexes. Suitable organophosphorous ligands include, for example, organophosphines, organophosphites, and organophosphoramidites. In certain embodiments, the ratio of CO to hydrogen is in the range of from 1:10 to 100:1, preferably of from 1:10 to 10:1. In certain embodiments, the hydroformylation reaction is conducted at a reaction temperature of from −25° C. to 200° C., preferably of from 50° C. to 120° C.

In certain embodiments, at least part of the product stream 90 is utilized in a downstream oxidation process. The oxidation process comprises contacting the methacrolein with an oxygen-containing gas in the presence of an oxidation catalyst under conditions sufficient to produce methacrylic acid. The oxidation process is known in the art, for example, as described in U.S. Pat. Nos. 9,751,822, 8,716,523, U.S. Patent Pub. No. 2016/0051970, and U.S. Pat. No. 7,999,133. The low amounts of methanol in the product stream 90 make it particularly advantageous as a source feed for the oxidation process. The molar ratio of oxygen to methacrolein employed in the oxidation process is not particularly limited, and may be conducted over a wide range of molar ratios such as from 1:10 to 1,000:1, preferably from 1:1 to 10:1. Oxygen-containing gases that are suitable for the oxidation process include, for example, oxygen gas, or a mixed gas comprising oxygen gas and a diluent inert to the reaction (e.g., nitrogen, carbon dioxide, and the like). In certain embodiments, air may be utilized as a suitable oxygen-containing gas for the oxidation process. Suitable oxidation catalysts include, for example, V, Mo, Cs, and Bi. The catalytic elements maybe supported on a carrier, for example, silica or alumina. In certain embodiments, the oxidation process is conducted at a reaction temperature of from 200° C. to 450° C., preferably of from 250° C. to 350° C.

In certain embodiments, at least part of the methacrylic acid produced by subjecting the product stream 90 to an oxidation process is utilized in a downstream esterification process. The esterification process comprises contacting the methacrylic acid with methanol in the presence of an esterification catalyst under reaction conditions sufficient to produce methyl methacrylate. The esterification process is known in the art, for example, as described in U.S. Pat. No. 3,821,286. The molar ratio of methanol to methacrylic acid employed in the esterification process is not particularly limited, and may be conducted over a wide range of molar ratios such as from 1:10 to 1,000:1, preferably from 1:1 to 10:1. Suitable esterification catalysts include, for example, sulfuric acid, sulfonic acids, ion exchange resins, lewis acids, and mixed metal polyacids. The catalytic elements maybe supported on a carrier, for example, silica or alumina. In certain embodiments, the esterification process is conducted at a reaction temperature of from 10° C. to 250° C., preferably of from 50° C. to 150° C.

Some embodiments of the invention will now be described in detail in the following Example.

EXAMPLES

Example 1

Preparation of Methacrylic Acid

A static mixer 29" long and 0.1315" inner diameter is used as a reactor. Dimethyl amine, acetic acid and water are mixed in a catalyst mixing vessel from which the outlet flow is 550 g/h containing 4.5 weight % dimethyl amine and an amount of acetic acid sufficient to maintain stream pH at 5.5. A stream comprising propionaldehyde and 37 weight % formaldehyde solution in water also containing 10-15% methanol (1:1 propionaldehyde:formaldehyde molar ratio) at a total flow of 1575 g/h is mixed with the aqueous catalyst solution and added to the reactor which is heated to 160° C. and maintained at 900 psig. An inhibitor solution containing 8 weight % 4-Hydroxy-TEMPO in water is added to the reactor at a flow rate of 20 g/h. The reactor outlet is cooled to 20° C., depressurized to 1 atm and is sent to a first phase separator with an internal temperature of 10° C. and pressure of 1 atm. The aqueous flow rate from the phase separator is 1471 g/h and contains 81 weight % water. The organic flow rate from the phase separator is 1487 g/h and contains greater than 90 weight % methacrolein. The aqueous phase is sent to a distillation column with 30 trays from which the overhead flow is 255 g/h consisting of 51 weight % methanol, 38 weight % methacrolein, and 11 weight % water. An inhibitor solution containing 8 weight % 4-Hydroxy-TEMPO in methanol is added to the condenser of the distillation column at a flow rate of 10 g/h. The side-draw flow from the distillation column is 650 g/h comprising greater than 99 weight % water. An inhibitor solution containing 8 weight % 4-Hydroxy-TEMPO in methanol is added to the side-draw receiver of the distillation column at a flow rate of 2 g/h. The bottoms stream from the distillation column contains recovered amine-acid catalyst which is recycled back to the catalyst mixing vessel at a fraction of 0.7. The distillate stream and 77.5 g/h of water are sent to a second phase separator. The aqueous phase from the second phase separator contains 40 weight % water and 49 weight % methanol. The organic phase flow from the second phase separator is 81 g/h and contains 89 weight % methacrolein. This organic phase from the first phase separator and the organic phase from the second phase separator are sent to a stripping column with 9 total trays at a total flow rate of 1487 g/h. The overhead vapors from the stripping column are condensed and recycled back to the phase separator. An inhibitor solution containing 8 weight % 4-Hyroxy-TEMPO in methanol is added to the condenser of the stripping column at a flow rate of 6 g/h. The bottoms stream from the stripping column is sent to a distillation column at a flow rate of 715 g/h with 22 trays wherein the overhead stream is sent to an oxidation step to produce methacrylic acid and the bottoms stream is sent to waste. The overhead stream consists of 99.3 weight % methacrolein, 0.4 weight % water, 0.1 weight % methanol, and less than 0.1 weight % combined undesired impurities (e.g., acetic acid, propionic acid, methacrolein dimer, and 2-methyl-2-pentenal) at a flow rate of 700 g/h. An inhibitor solution containing 8 weight % 4-Hyroxy-TEMPO in methanol is added to the condenser of the distillation column at a flow rate of 10 g/h.

The example demonstrates that the process of this invention is effective at removing methanol and other detrimental impurities from a stream containing methacrolein prepared by a Mannich condensation process, such that the methacrolein stream has a low methanol content not previously achieved by the various methods of the prior art. The low methanol and impurity content of the methacrolein stream makes it suitable for use in a downstream oxidation process of the methacrolein.

What is claimed is:

1. A process for preparing methacrolein comprising:
   (a) mixing water and an amine-acid catalyst to provide a catalyst stream;
   (b) sending the catalyst stream and a reaction stream comprising propionaldehyde, formaldehyde, and methanol to a reactor to produce a first intermediate stream comprising methacrolein, methanol, and at least 8 weight % water;
   (c) providing the first intermediate stream to a first phase separator to produce (i) a first aqueous phase comprising methacrolein, methanol, amine-acid catalyst, and at least 65 weight % water, and (ii) a first organic phase comprising water, at least 85 weight % methacrolein, and less than 5 weight % methanol;
   (d) distilling the first aqueous phase in a first distillation column to produce (i) a second intermediate stream comprising methacrolein, water, and less than 60 weight % methanol, (ii) a bottoms stream comprising amine-acid catalyst, and (iii) a side draw stream comprising methanol and water;
   (e) providing the second intermediate stream and water to a second phase separator to produce (i) a second organic phase comprising methacrolein, water, and less than 55 weight % methanol, and (ii) a second aqueous phase;
   (f) distilling the first organic phase and the second organic phase in a second distillation column to produce (i) a third intermediate stream comprising methacrolein and less than 2 weight % methanol, and (ii) an overhead stream;
   (g) distilling the third intermediate stream in a third distillation column to produce (i) a product stream comprising methacrolein and water in a combined amount of at least 97 weight %, less than 2 weight % methanol, and less than 1 weight % of impurities comprising one or more of acetic acid, propionic acid, methacrolein dimer, and 2-methyl-2-pentenal, and (ii) a waste stream;
   (h) recycling at least part of the overhead stream to the first phase separator; and
   (i) recycling at least part of the bottoms stream to the catalyst stream.

2. The process of claim 1, wherein the propionaldehyde is produced by contacting ethylene with CO and $H_2$ in the presence of a hydroformylation catalyst.

3. The process of claim 1, further comprising providing at least part of the product stream to a process comprising contacting the methacrolein with an oxygen-containing gas in the presence of an oxidation catalyst to produce methacrylic acid.

4. The process of claim 3, further comprising providing the methacrylic acid to a process comprising contacting the methacrylic acid with methanol in the presence of an esterification catalyst to produce methyl methacrylate.

5. The process of claim 2, further comprising providing at least part of the product stream to a process comprising contacting the methacrolein with an oxygen-containing gas in the presence of an oxidation catalyst to produce methacrylic acid.

6. The process of claim 5, further comprising providing the methacrylic acid to a process comprising contacting the methacrylic acid with methanol in the presence of an esterification catalyst to produce methyl methacrylate.

7. The process of claim 1, wherein the first phase separator is operated at a temperature of less than 15° C.

8. The process of claim 1, wherein the second phase separator is operated at a temperature of less than 25° C.

9. The process of claim 1, wherein the ratio of the water entering the second phase separator to the second intermediate stream entering the second phase separator is from 1:10 to 100:1.

10. The process of claim 1, wherein the ratio of the third intermediate stream exiting the second distillation column to the combined amount of first organic phase and the second organic phase entering the second distillation column is from 1:10 to 9:10.

* * * * *